(12) United States Patent
Kals

(10) Patent No.: US 8,670,834 B2
(45) Date of Patent: Mar. 11, 2014

(54) OPTIMAL MODEL CONSTANTS FOR SIMULTANEOUS STIMULATION WITH CHANNEL INTERACTION COMPENSATION

(75) Inventor: Mathias Kals, Innsbruck (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/469,343

(22) Filed: May 11, 2012

(65) Prior Publication Data

US 2012/0303094 A1    Nov. 29, 2012

Related U.S. Application Data

(60) Provisional application No. 61/485,726, filed on May 13, 2011.

(51) Int. Cl.
*A61N 1/00*    (2006.01)

(52) U.S. Cl.
USPC .......................................... 607/57

(58) Field of Classification Search
USPC .................................... 607/55–57
See application file for complete search history.

(56) References Cited

U.S. PATENT DOCUMENTS

2006/0247735 A1 * 11/2006 Honert ............................ 607/57
2009/0036962 A1 *  2/2009 Zierhofer ...................... 607/137

* cited by examiner

*Primary Examiner* — Scott Getzow
(74) *Attorney, Agent, or Firm* — Sunstein Kann Murphy & Timbers LLP

(57) ABSTRACT

Approaches are described for fitting a simultaneous stimulation arrangement of a cochlear implant system to an implanted patient. Electrode contacts in an electrode array implanted in a patient cochlea are stimulated with a fitting pattern of stimulation signals. Then current spread decay parameters are determined for patient specific amplitude compensation of the simultaneous stimulation arrangement based on either a psychoacoustic aspect or an objective measurement of patient percept to the fitting pattern.

17 Claims, 6 Drawing Sheets

OPTIMAL MODEL CONSTANTS FOR SIMULTANEOUS STIMULATION WITH CHANNEL INTERACTION COMPENSATION

This application claims priority from U.S. Provisional Patent Application 61/485,726, filed May 13, 2011 and incorporated herein by reference.

TECHNICAL FIELD

The present invention relates to medical implants, and more specifically to fit customization in audio prosthesis systems such as cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency->electrode mapping
Parameters describing the electrical field distribution One common method for fit adjustment is to behaviorally find the threshold (THR) and most comfortable loudness (MCL) value for each separate electrode contact. See for example, Rätz, *Fitting Guide for First Fitting with MAESTRO 2.0*, MED-EL, Furstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL (most comfortable loudness) is reached.

One approach for an objective measurement of MCLs and THLs is based on the measurement of the ECAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the super-position of single neural responses at the outside of the axon membranes. The amplitude of the ECAP at the measurement position is between 10 µV and 1800 µV.

In natural hearing, incoming sounds simultaneously stimulate the cells within the cochlea. Some cochlear implant systems simultaneously stimulate the electrode contacts, but this gives rise to spatial channel interaction from overlap of the stimulation fields at each electrode contact by superpositioning of simultaneous current spreads across the electrode array. This represents a meaningful obstacle for optimal sound perception in the implant patient. One way to reduce spatial channel interaction is to use sequential stimulation of the electrode contacts where the electrode contacts are stimulated one at a time and there is no superposition of electric currents. Another way to retain simultaneous stimulation and still reduce spatial channel interaction is described in U.S. Pat. No. 6,594,525 (incorporated herein by reference) using an approach known as Channel Interaction Compensation (CIC). CIC calculates channel interaction compensated amplitudes for simultaneous stimulation. Two current spread decay constants are used, current spread decay in the apical direction is modeled by $\alpha$, and that in the basal direction is modeled by $\beta$.

U.S. Provisional Patent Application 61/382,996, filed Sep. 15, 2010 and incorporated herein by reference, describes accelerated fitting of simultaneously stimulated cochlear implants based on current spread. A first electrode contact is fit to the patient by determining the MCL value, and then the MCL for each remaining unfit stimulation electrode is determined. The current spread characteristics are represented by an exponential decay function based on a voltage profile measured along the electrode array. Setting the CIC parameters α and β to arbitrary values (e.g., in the range [0.70-0.80]) provides acceptable performance in speech reception but studies have shown that patient-specific values would be an improvement.

SUMMARY

Embodiments of the present invention are directed to fitting a simultaneous stimulation arrangement of a cochlear implant system to an implanted patient. Electrode contacts in an electrode array implanted in a patient cochlea are stimulated with a fitting pattern of stimulation signals. Then current spread decay parameters are determined for patient specific amplitude compensation of the simultaneous stimulation arrangement based on either a psychoacoustic aspect of patient percept to the fitting pattern.

The decay parameters may include an apical decay parameter and a basal decay parameter. The fitting pattern may be based on repeating a given acoustic signal alternately using sequential stimulation and simultaneous stimulation of the electrode contacts. In that case, the decay parameters may be adjusted to provide the same patient percept for sequential stimulation and simultaneous stimulation. The fitting pattern also may be presented based on an alternative forced choice process, based on making fixed step changes in the decay parameters, based on making factor changes in the decay parameters, and/or based on changing loudness and timbre of the stimulation signals. Determining the decay parameters may be further based on determining electrode contact masking profiles, for example, using an exponential fit of the masking profiles for determining the decay parameters.

Embodiments of the present invention are directed to fitting a simultaneous stimulation arrangement of a cochlear implant system to an implanted patient. Electrode contacts in an electrode array implanted in a patient cochlea are stimulated with a fitting pattern of stimulation signals. Then current spread decay parameters are determined for patient specific amplitude compensation of the simultaneous stimulation arrangement based on an objective measurement of patient percept to the fitting pattern.

The objective measurement may include telemetric measurement of voltages at the electrode contacts, for example, using a telemetry voltage matrix for determining the decay parameters. The objective measurement also may include electrically evoked compound action potential (ECAP) measurement, for example, using an ECAP growth function and/or an ECAP exponential least square fit for determining the decay parameters. The objective measurement also may include electrically evoked stapedius reflex (ESRT) measurement.

Embodiments also include a cochlear implant fitting system using a method according to any of the above, and a computer program product implemented in a computer readable storage medium for fitting an implanted electrode of a cochlear implant to an implanted patient and including program code for performing a method according to any of the above.

DETAILED DESCRIPTION

Embodiments of the present invention are directed to a method and a system for the fitting of each electrode contact in a simultaneous stimulation system. Instead of using arbitrary predefined values for the model parameters, a patient-specific estimation based on psychoacoustic aspects and/or objective measurement is utilized. Several specific arrangements for CIC-parameter identifications are provided which can determine correct parameter sets for the specific cochlear implant patient.

Figure 1:
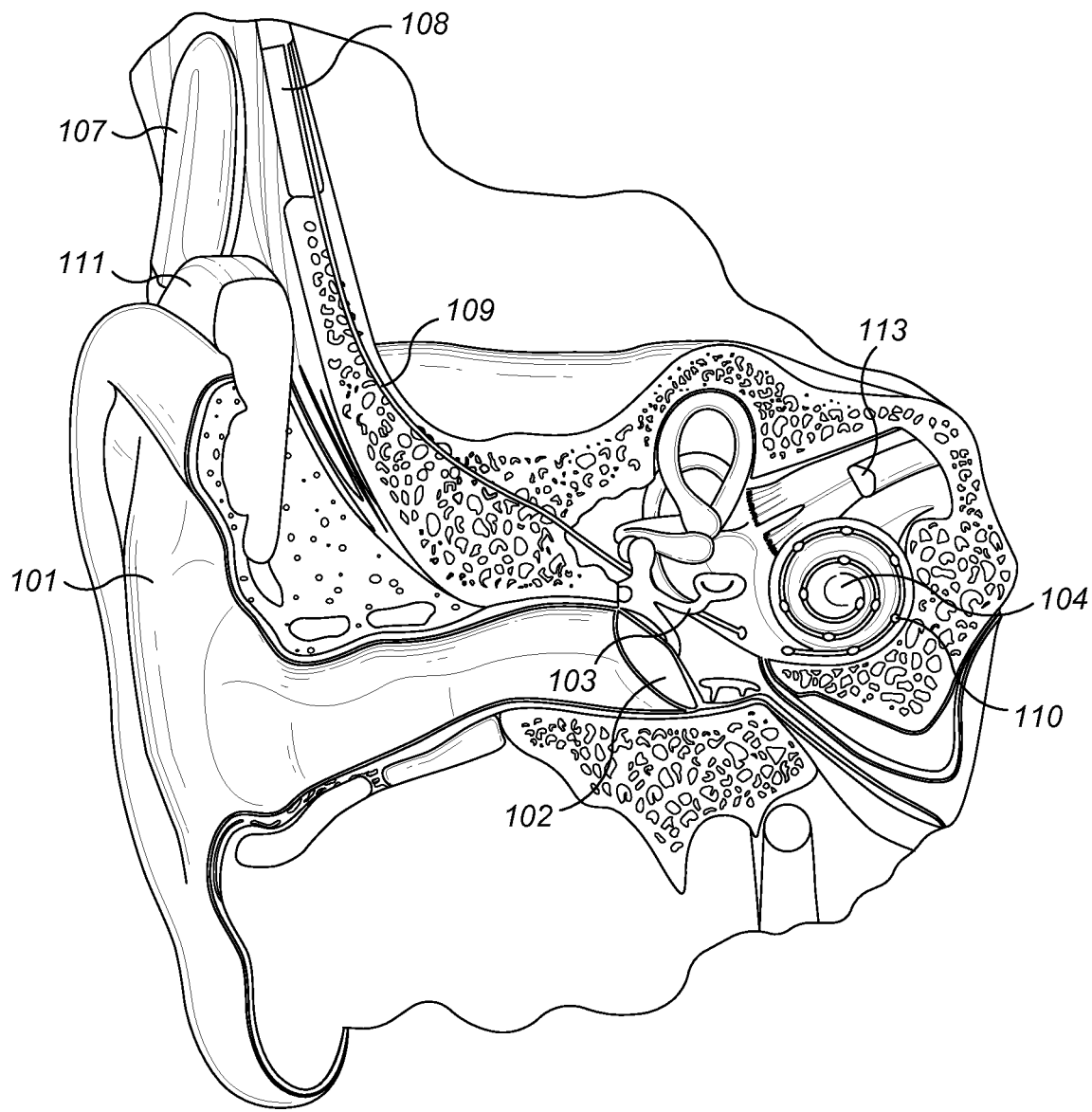
FIG. 1 shows anatomical structures in a human ear having a cochlear implant system.
Figure 2:
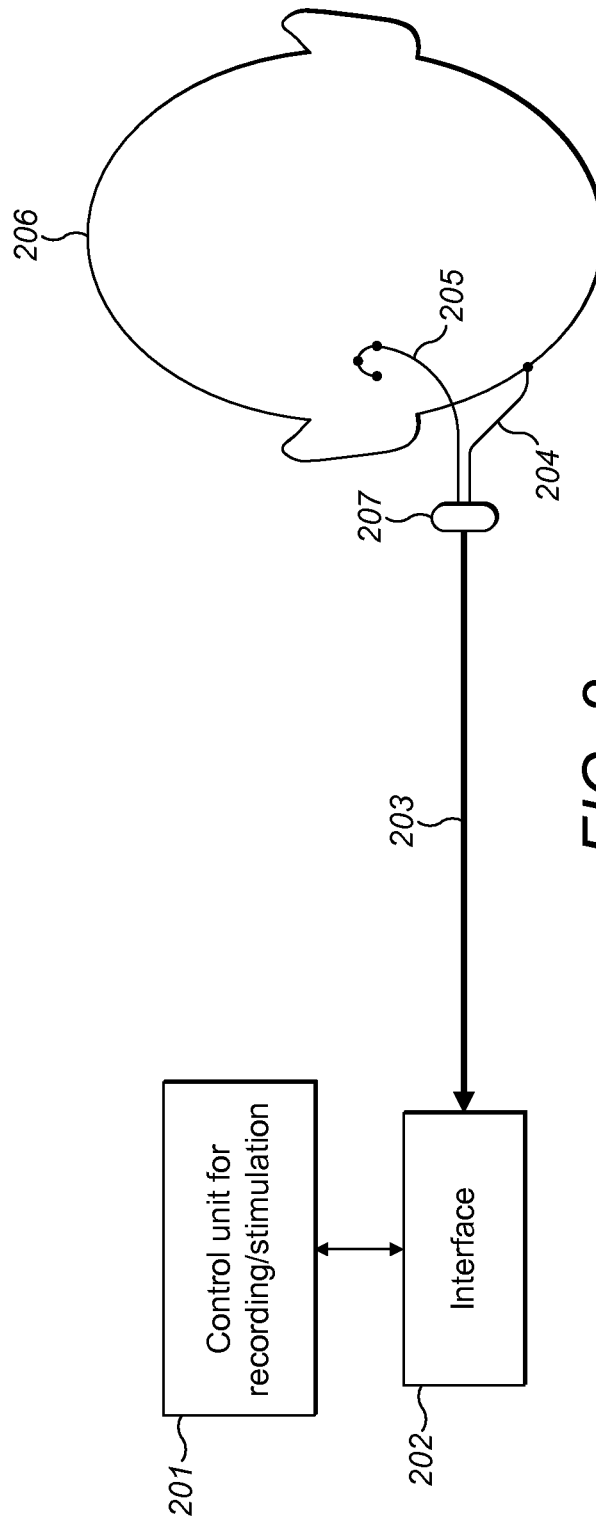
FIG. 2 shows a block diagram of a cochlear implant fitting system according to one specific embodiment of the present invention.

FIG. 2 shows a block diagram of a cochlear implant fitting system according to one specific embodiment of the present invention. Control Unit 201 for Recording and Stimulation, for example, a Med-E1 Maestro CI system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After delivering a stimulation pulse, a Cochlear Implant Electrode 204 may be used as a sensing element to determine relative values of current and voltage characteristics of the adjacent tissue, for example, for use measuring current spread.

Control Unit 201 fits a first unfit Cochlear Implant Electrode 204 to the patient by determining a most comfortable loudness (MCL) value for that electrode. Control Unit 201 then determines an MCL value for each remaining unfit Cochlear Implant Electrode 204 starting from an initial fitting current based on current spread characteristics of at least one already fit Cochlear Implant Electrode 204.

US 2009036962 describes one specific possible current spread model where the spread decays approximately exponentially and can be expressed by:

$$I(x) = I\exp\left(-\frac{x}{\lambda}\right) \quad \text{(Eq. 1)}$$

where I(x) is the current at some distance x from stimulus I, and λ, is a decay constant. For electrode arrays with equidistant distance d between the electrode contacts, the decay on next neighboring electrode can be expressed as in Equation 2 by an exponential function with base α:

$$\frac{I(x=d)}{I(0)} = \exp\left(-\frac{d}{\lambda}\right) = \alpha \quad \text{(Eq. 2)}$$

By reason of the geometrical structure (narrowing tube), two exponential constants in directions apical ($\alpha$) and basal ($\beta$) respectively model the electrode current spread. (Note that the discussion herein works equally effectively interchanging $\alpha$ and $\beta$.) The resulting current at the location of electrode m when electrode n is stimulated with current $I_n$ is given by:

$$I_{n,m} = I_n \alpha^{|n-m|} \text{ for } m<n, \text{ and}$$

$$I_{n,m} = I_n \beta^{|n-m|} \text{ for } m \geq n \quad \text{(Eq. 3)}$$

For example, for an electrode spacing of d=2.4 mm, $\alpha$ and $\beta$ are typically around 0.75 and 0.70 respectively. Telemetry measurements can be taken inside the cochlea to measure the voltage profile along the electrode array when a stimulus pulse is applied on the electrode array. The two decay constants are reflected in the measured voltage profile and can then be assessed in each individual patient.

Psychoacoustic Methods:

When CIC parameters are optimal for a given patient, then simultaneous stimulation, the sound percept is very similar to that produced with sequential stimulation. Based on this idea, a sound processor repeatedly presents an acoustic fitting signal while switching between sequential stimulation and simultaneous stimulation, both using same clinical settings (MCL, THR, filter-bank and maplaw). During this, the CIC current spread decay constant model parameters are adjusted until the sound percept for both stimulation modes best match.

Figure 3:
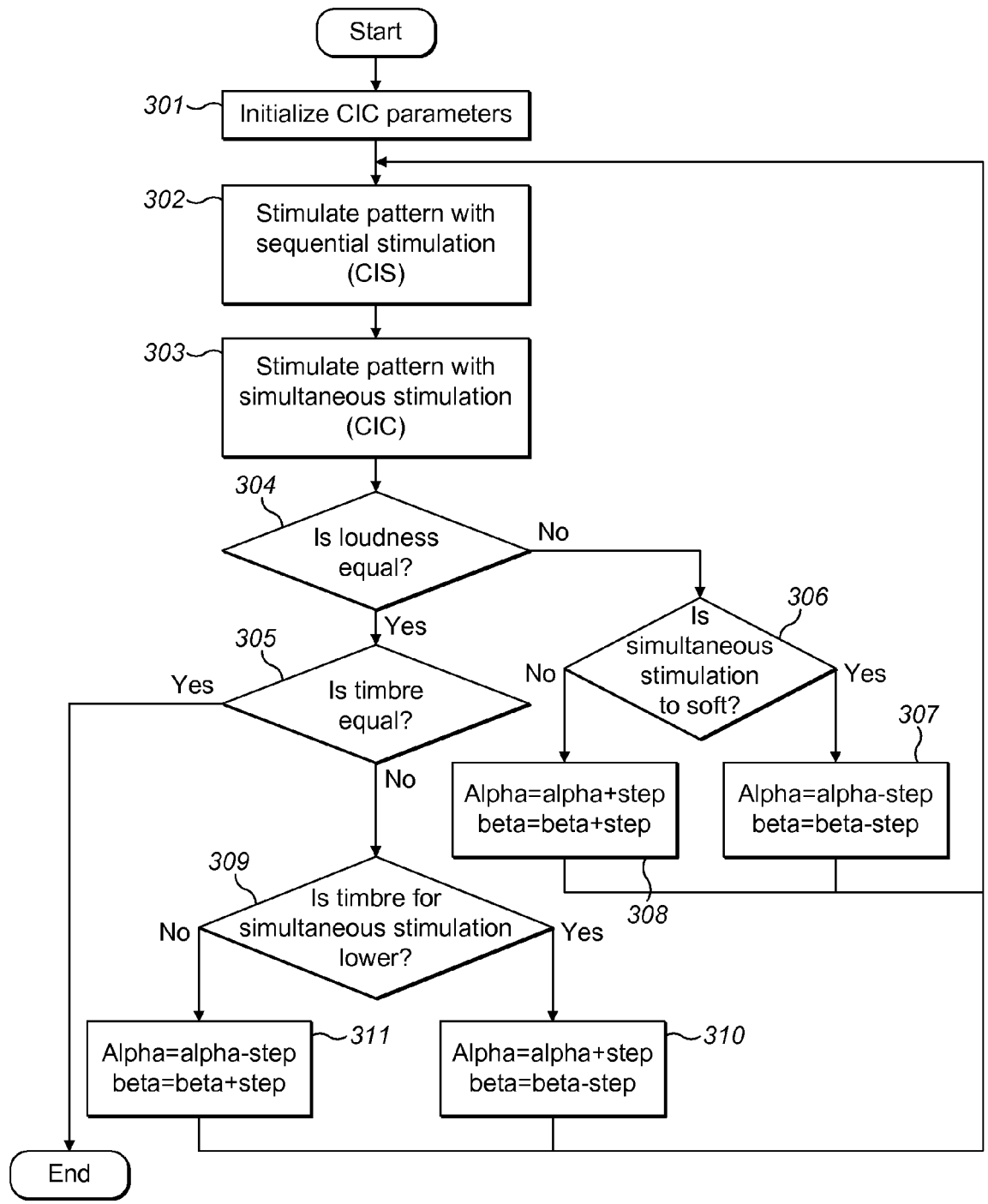
FIG. 3 shows various steps in a psychoacoustic identification of decay parameters according to an embodiment of the present invention.

FIG. 3 shows various steps in a psychoacoustic identification of decay parameters using a series of step adjustments. First, step 301, the decay constant parameters may be initialized with high values, e.g., $\alpha = \beta = 0.99$. A fitting pattern of stimulation signals is then sequentially applied to the electrode contacts, step 302, for example using CIS stimulation, after which, the same fitting pattern of stimulation signals is simultaneously applied to the electrode contacts, step 303, for example using CIC stimulation. The loudness of the fitting pattern of stimulation signals is adjusted to be comfortably loud for the sequential stimulation, and for the fitting pattern of stimulation signals, broad-band noise (e.g. white noise), any appropriate speech, music sample or stimulation patterns can be used.

When the loudness percept and the timbre percept are equally loud for both sequential and simultaneous stimulation, steps 304 and 305, the system is optimally fit to the patient. If the simultaneous stimulation loudness is too soft, step 306, then the decay constant parameters, $\alpha$ and $\beta$, can be decreased by subtracting a fixed step amount (e.g., 0.05 or 0.025), step 307. Otherwise, if the simultaneous stimulation loudness is not too soft, step 306, then the decay constant parameters, $\alpha$ and $\beta$, can be increased by adding a fixed step amount. Or, if the loudness percepts are equal, but the timbre percepts are different, step 309, then if the simultaneous stimulation timbre percept is lower, the apical decay constant $\alpha$ is increased by a fixed step amount while the basal decay constant $\beta$ is decreased by a fixed step amount, step 310. Otherwise, if the simultaneous stimulation timbre percept is higher, the apical decay constant $\alpha$ is decreased by a fixed step amount while the basal decay constant $\beta$ is increased by a fixed step amount, step 311. Once the decay constants have been adjusted, the process is repeated starting with steps 302 and 303.

Various other specific methods could be used instead of fixed step adjustments, for example, an alternative forced choice (AFC) procedure. Instead of adding and subtracting a fixed step amount, the decay constant parameters can also be adjusted by multiplying with a specific factor (e.g., 0.95 and 1.05 for a decrease and increase, respectively). The process shown in FIG. 3 can be used for a configuration which contains all channels/electrodes, or with only a subset of the electrodes, for example, a pair of simultaneous electrodes. In both stimulation strategies, the same electrodes with identical stimulation frame rate should be used to avoid unwanted side effects. And depending on the circumstances, it may be possible for such a fit process to be performed just by the implanted patient, or with support from an audiologist.

Another psychoacoustic fit approach may be based on a masker and probe signal arrangement. A fitting pattern in the form of a masker stimulus can be presented on an electrode contact at a perceptible level (within THR and MCL) with desired clinical pulse parameters (e.g., pulse-rate and pulse-phase duration). After that, on a different electrode contact, the fitting pattern can continue with a subsequent probe stimuli. If both the masker and probe stimuli are applied within the absolute refractory time of auditory nerves ($t_a \leq 1$ ms), then a masking profile can be recorded along the electrode contacts. The probe stimulus can be increased starting from zero or any other appropriate starting point on each other electrode contact until a perceptible difference can be perceived by the implant patient. This can be done via an AFC approach, a fixed step method of adjustment or any other appropriate method. After normalization of the recorded masking profiles with the masker level, an exponential fit delivers the desired CIC parameters. Between the masker probe intervals a time interval of at least the complete refractory period ($t_c \geq 10$ ms) may need to be passed to exclude temporal masking effects.

Figure 4:
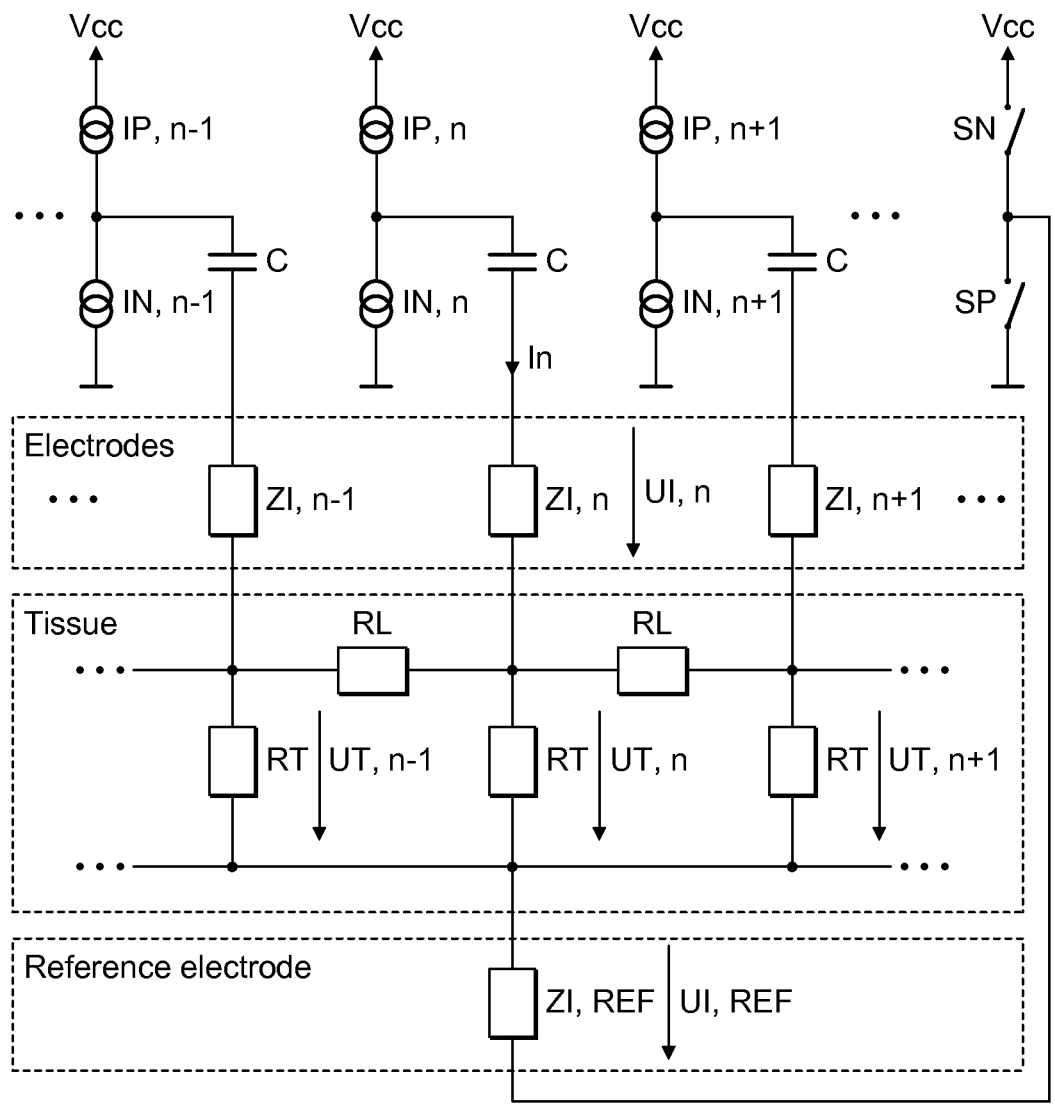
FIG. 4 shows an equivalent network for a cochlea and electrode contacts.

Objective Methods:

Besides psychoactive methods, other embodiments of the present invention may be based on using objective testing measurements, for example, telemetry voltages. Current cochlear implants allow the voltages on each electrode contact to be measured at the moment of stimulation. FIG. 4 shows a simple equivalent circuit for cochlear tissue and electrode contacts. For convenience the cochlear tissue is represented by a simple resistive ladder $R_L$ and $R_T$ where T denotes transversal and L longitudinal directions in the tissue layer that models the fluid filled scala tympani. The voltage on resistors $R_T$ is given by:

$$U_{T,n+m} = U_{T,n-m} = \alpha^{|m|} U_{T,n}, \quad \text{(Eq. 4)}$$

where m indicates the distance to a simulating segment n in segments/electrodes and $\alpha$ the current decay per electrode. This means that if, for example, on segment n=6 a voltage of $U_{T,6}$ is present, then on segment 8 and 4 a voltage results of: $U_{T,8} = U_{T,4} = \alpha^2 U_{T,6}$. The exponential base $\alpha$ can be expressed just with resistors $R_T$ and $R_L$ by:

$$\alpha = 1 - 2R_L/(R_L + \text{sqrt}(R_L^2 + 4R_T R_L)). \quad \text{(Eq. 5)}$$

Since the impedances $Z_I$ and $Z_{I,REF}$ (transition between metal electrode contact surface and the intracochlear fluid) in the layers 'Electrodes' and 'Reference Electrode' respectively are complex and the resulting voltages $U_I$ and $U_{I,REF}$ are frequency dependent. Consequently, these impedances influence the measured voltages on the electrode contacts. On an active electrode contact, the resulting voltage $U_M$ relative to the reference electrode is:

$$U_{m,n} = U_{I,n} + U_{T,n} U_{I,REF}. \quad \text{(Eq. 6)}$$

On other electrode contacts, the resulting voltage relative to the reference electrode is only:

$$U_{M,n+m} = U_{M,n-m} = \alpha^{|m|} U_{T,n} + U_{I,REF} = \alpha^{|m|}(U_{T,n} + U_{I,REF}/\alpha^{|m|}).$$ (Eq. 7)

Figure 5:
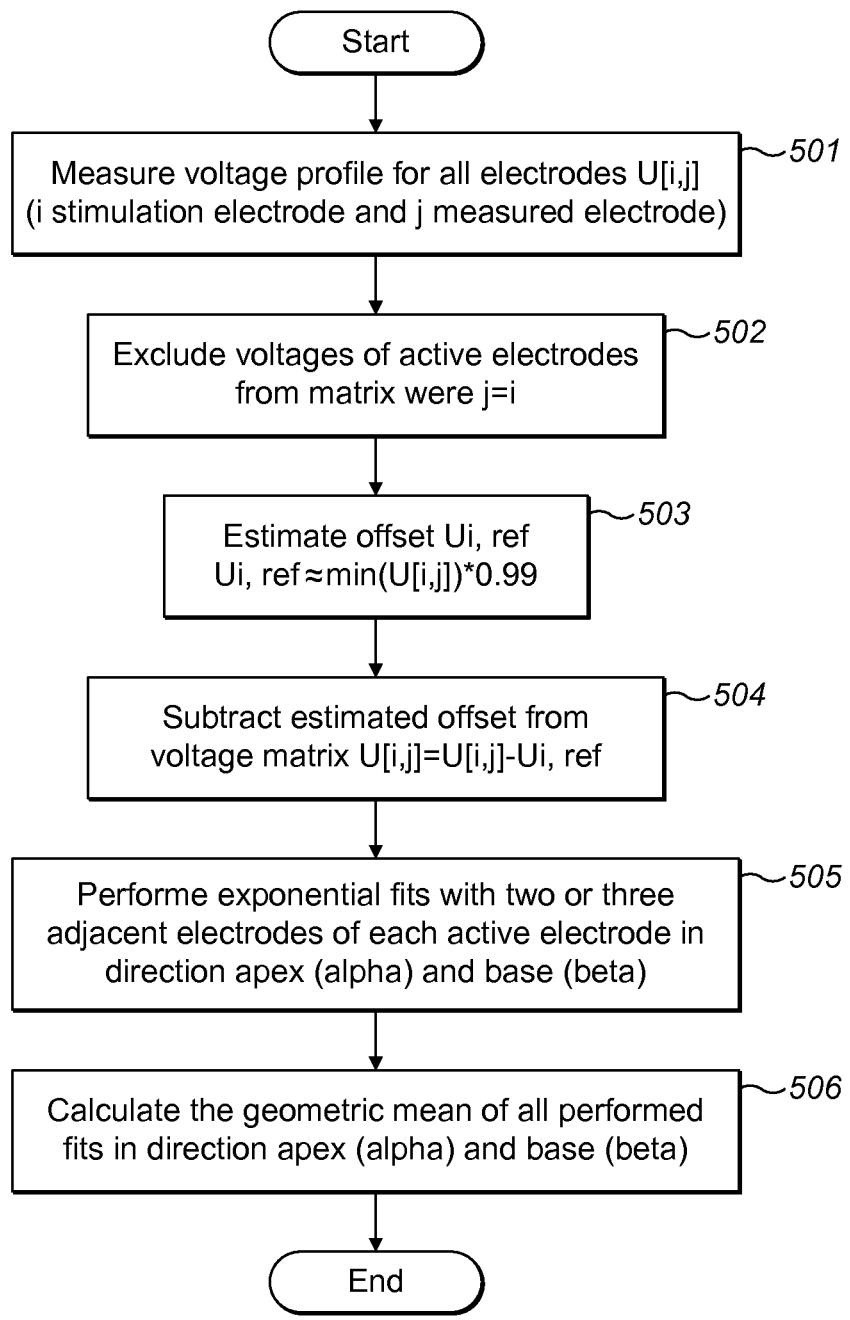
FIG. 5 shows various steps in an objective measurement of decay parameters according to an embodiment of the present invention.

For determining optimal CIC parameters, the voltage profile in the layer 'Tissue' is of interest since the exponential decay is reflected in these voltages as shown in Equation 4. FIG. 5 shows various logical steps in an algorithm for objectively determining desired CIC parameters based on a telemetry voltage matrix. First, step 501, a voltage matrix profile is measured for all electrode contacts where the row index i represents the position of the stimulation electrode contact and the column index j indicates the position of the measuring electrode contacts during stimulation. This stimulation and the measurements are performed by the implant and the results are transferred outside via RF-link from the implant. The voltages of active electrode contacts are excluded, step 502, because $U_{T,n}$ is electrode dependent and varies from one electrode contact to another.

The influence of an electrode offset voltage in the measured telemetry voltage matrix can be minimized next, step 503. The electrode offset voltage $U_{I,REF}$ can be assumed to be constant if all electrode contacts use the same stimulus signal (pulse amplitude and pulse-phase duration) and the same measurement time. In one approach, the offset voltage $U_{I,REF}$ can be estimated based on the telemetry voltage matrix U. For example, the lowest measured voltage $U_{min}$ can be used as an approximation for $U_{I,REF}$. Based on an exponential decay and constant $U_T$ this voltage is given by:

$$U_{min} = U_T \min(\alpha^{N-1}, \beta^{N-1}) + U_{I,REF}$$ (Eq. 8)

were N denotes the number of electrodes. If typical values are assumed for the current decay constants, a and/, e.g. 0.70 and 0.65 respectively, in a N=12 channel system $U_{min} = U_T 0.00875 + U_{I,REF}$. With a realistic assumption that $U_{I,REF} \approx U_T$ we can write:

$$U_{I,REF} \approx U_{min}/(0.00875+1) = U_{min} 0.99 = U_0$$ (Eq. 9)

The electrode offset voltage $U_{I,REF}$ influences the outcome of the upcoming fitted exponential decay constants, and generally, a high offset voltage reduces the magnitude of established decay constants in a least square fit procedure. In telemetry measurements only the magnitude of the complex voltages are measured at a specific time point, therefore the magnitude of the complex voltage $U_{I,REF}$ is described by $U_{I,REF}$ for simplification.

Once the offset voltage $U_{I,REF}$ is determined, it is subtracted from the voltage matrix voltages, step 504: $U_{[i,j]} = U_{[i,j]} - U_{I,ref}$. Following that, an exponential fit procedure is performed, step 505. Only the closest two or three adjacent neighbors of an active electrode contact in each direction (apex and base) are used because in these voltages the best SNR is given and a faulty offset estimation of $U_0$ leads to the least influence to the estimated CIC parameters, as shown in Equation 7. Finally, the global current decay constants, α and β, can be calculated, for example, as the geometric means of all individual performed fits in each respective direction, step 506.

In another approach, the derivative $U_{M,n+m}'$ of the voltage profile $U_{M,n+m}$ can be used where consequently an included offset voltage $U_{I,REF}$ disappears as shown in Equations 10 and 11:

$$U_{M,n+m} = U_{T,n}\alpha^m + U_{I,REF}$$ (Eq. 11)

$$U_{M,n+m}' = U_{T,n} ln(\alpha)\alpha^m$$ (Eq. 11)

By dividing the derivative values $U_{M,n+m+1}'/U_{M,n+m}'$ only the apical current decay constant α remains. In the same fashion the basal decay constant β can be derived. And again the global α and β can be calculated by geometric averaging of the individual results.

Patient-specific simultaneous-stimulation current spread decay constants may also be determined from other objective measurements such as electrically-evoked compound action potentials (eCAP) and electrically evoked stapedius reflex thresholds (eSRT). Typically, an eCAP growth function (eCAP voltages as a function of stimulus level) increases approximately linearly starting from some threshold $eCAPT_s$ (where s denotes the position of the electrode contact) which can be used for estimating CIC parameters such as the current spread decay constant. In the following, for a grouping of simultaneous electrode contacts, a syntax is used where the contained electrode contacts are enclosed by squared brackets.

At first, two electrode contacts s and s+2 are stimulated simultaneously with $[x_\beta A_s A_{s+2}]$ where $A_s = A_{s+2} = eCAPT_{s+1}$ and while parameter $x_\beta$ is increased from zero until on electrode contact s+1 an eCAP response occurs. Then electrode contacts s and s+2 are stimulated again simultaneously with $[A_s x_\alpha A_{s+2}]$ while parameter $x_\alpha$ is increased from zero until on electrode contact s+1 an eCAP occurs. Based on these measurements the amplitude on the measured electrode contact s+1 can be expressed by:

$$eCAPT_{s+1} = \beta_s x_\beta A_s + \alpha_{s+2} A_{s+2} = \beta_s A_s + \alpha_{s+2} x_\alpha A_{s+2} = A_{s+1}.$$ (Eq. 12)

Solving this linear equation results in:

$$\alpha_{s+2} = (x_\beta - 1)/(x_\beta x_\alpha - 1) \text{ and } \beta_s = (x_\alpha - 1)/(x_\beta x_\alpha - 1).$$ (Eq. 13)

The $eCAPT_{s+1} = A_{s+1}$ from the run increasing $x_\beta$ can be assumed to be the same as for the run increasing $x_\alpha$, and $A_s = A_{s+2} = eCAPT_{s+1}$ for the run increasing $x_\alpha$. The same principle can be utilized using eSRT levels instead of eCAP levels.

Figure 6:
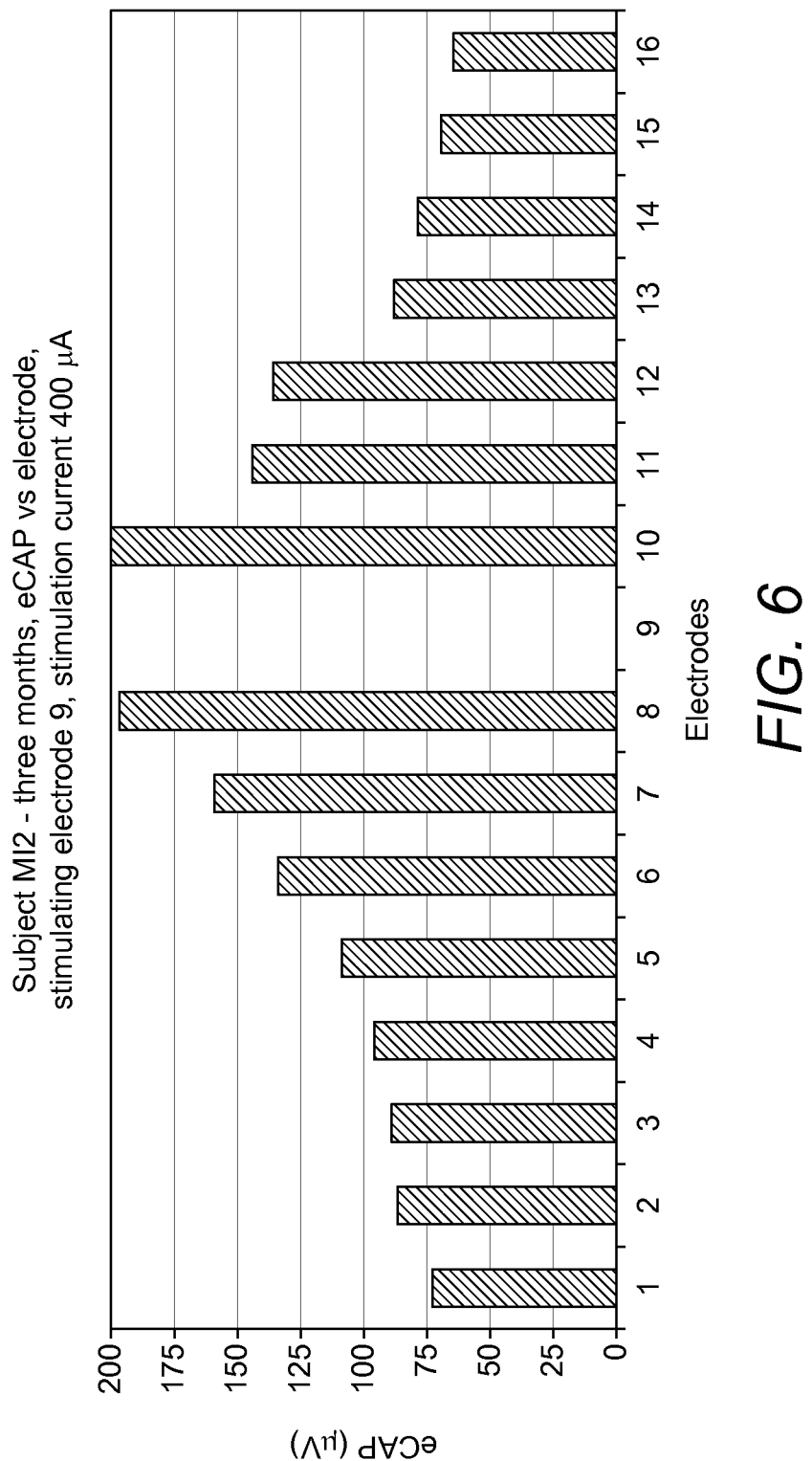
FIG. 6 shows a graph of eCAP amplitudes (spread of excitation) decaying exponentially in apical and basal directions.

Another non-simultaneous stimulation approach stimulates one electrode contact at a level (about the comfortable loudness level) where eCAPs are detectable on all other electrode contacts. The resulting eCAP amplitudes (spread of excitation) decay exponentially in direction apex and base as shown in FIG. 6. Since eCAP amplitudes are a function of the number of elicited action potentials, they reflect also the amount of neuronal survival. To exclude the influence (e.g. dead regions) the measured spread of excitation $eCAP_{s,m}$ (where index s indicates the number of stimulation electrode and m of measured electrode) has to be normalized by the eCAPT by:

$$eCAPN_{s,m} = eCAP_{s,m}/eCAP_m.$$ (Eq. 14)

With these normalized amplitudes an exponential least square fit can be performed directly without an offset correction as used in the previous described method. Since the eCAP measurements were performed on a separate reference electrode, were no stimulation occurs. As in the previous described method only the closest two or three neighbors of an active electrode in direction apex and base are used in the fit procedure. The global α and β is calculated by geometric averaging of the individual results in both approaches.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for fitting a simultaneous stimulation arrangement of a cochlear implant system to an implanted patient, the method comprising:
    stimulating with a fitting pattern of stimulation signals a plurality of electrode contacts in an electrode array implanted in a patient cochlea; and
    determining a plurality of current spread decay parameters for patient specific amplitude compensation of the simultaneous stimulation arrangement based on a psychoacoustic aspect of patient percept to the fitting pattern.

2. A method according to claim 1, wherein the fitting pattern is presented based on an alternative forced choice process.

3. A method according to claim 1, wherein the fitting pattern is presented based on making fixed step changes in the decay parameters.

4. A method according to claim 1, wherein the fitting pattern is presented based on making factor changes in the decay parameters.

5. A method according to claim 1, wherein the fitting pattern is presented based on changing loudness and timbre of the stimulation signals.

6. A method according to claim 1, wherein the decay parameters include an apical decay parameter and a basal decay parameter.

7. A method according to claim 1, wherein the fitting pattern is based on repeating a given acoustic signal alternately using sequential stimulation and simultaneous stimulation of the electrode contacts.

8. A method according to claim 7, wherein the decay parameters are adjusted to provide the same patient percept for sequential stimulation and simultaneous stimulation.

9. A method according to claim 1, wherein determining the decay parameters is further based on determining electrode contact masking profiles.

10. A method according to claim 9, wherein an exponential fit of the masking profiles is used for determining the decay parameters.

11. A method for fitting a simultaneous stimulation arrangement of a cochlear implant system to an implanted patient, the method comprising:
    stimulating with a fitting pattern of stimulation signals a plurality of electrode contacts in an electrode array implanted in a patient cochlea; and
    determining a plurality of current spread decay parameters for patient specific amplitude compensation of the simultaneous stimulation arrangement based on objective measurement of patient percept to the fitting pattern.

12. A method according to claim 11, wherein the objective measurement includes telemetric measurement of voltages at the electrode contacts.

13. A method according to claim 12, wherein a telemetry voltage matrix is used for determining the decay parameters.

14. A method according to claim 11, wherein the objective measurement includes electrically evoked compound action potential (ECAP) measurement.

15. A method according to claim 14, wherein an ECAP growth function is used for determining the decay parameters.

16. A method according to claim 14, wherein an ECAP exponential least square fit is used for determining the decay parameters.

17. A method according to claim 14, wherein the objective measurement includes electrically evoked stapedius reflex (ESRT) measurement.

* * * * *

UNITED STATES PATENT AND TRADEMARK OFFICE
CERTIFICATE OF CORRECTION

| | |
|---|---|
| PATENT NO. | : 8,670,834 B2 |
| APPLICATION NO. | : 13/469343 |
| DATED | : March 11, 2014 |
| INVENTOR(S) | : Mathias Kals |

It is certified that error appears in the above-identified patent and that said Letters Patent is hereby corrected as shown below:

In the Claims:

In Col. 10, line 52
replace "claim 14"
with --claim 11--

Signed and Sealed this
Tenth Day of June, 2014

Michelle K. Lee
*Deputy Director of the United States Patent and Trademark Office*